United States Patent
Lee et al.

(10) Patent No.: US 10,474,133 B2
(45) Date of Patent: Nov. 12, 2019

(54) INSPECTION DEVICE FOR INSPECTING WAFER AND METHOD OF INSPECTING WAFER USING THE SAME

(71) Applicant: SAMSUNG ELECTRONICS CO., LTD., Suwon-si, Gyeonggi-do (KR)

(72) Inventors: Janghee Lee, Seoul (KR); Yoo Jin Jeong, Suwon-si (KR); Sangbong Park, Yongin-si (KR); Byeonghwan Jeon, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 73 days.

(21) Appl. No.: 15/724,758

(22) Filed: Oct. 4, 2017

(65) Prior Publication Data
US 2018/0150057 A1 May 31, 2018

(30) Foreign Application Priority Data
Nov. 29, 2016 (KR) .................. 10-2016-0160761

(51) Int. Cl.
*G05B 19/4097* (2006.01)
*G01N 21/95* (2006.01)
(Continued)

(52) U.S. Cl.
CPC ..... *G05B 19/4097* (2013.01); *G01N 21/9501* (2013.01); *G03F 7/7065* (2013.01); *G03F 7/70516* (2013.01); *G03F 7/70533* (2013.01); *H01L 22/12* (2013.01); *H01L 22/20* (2013.01); *G05B 2219/45031* (2013.01); *H01L 21/67288* (2013.01)

(58) Field of Classification Search
CPC ........... G01N 21/9501; G03F 7/70516; G03F 7/70533; G05B 19/4097; G05B 2219/37224; G05B 2219/45031; H01L 21/67288; H01L 22/20
See application file for complete search history.

(56) References Cited

U.S. PATENT DOCUMENTS 5,808,735 A 9/1998 Lee et al.
7,020,350 B2 3/2006 Sakai et al.
(Continued)

FOREIGN PATENT DOCUMENTS

| JP | 2013234976 A | 11/2013 |
| KR | 10-2012-0105863 | 9/2012 |
| KR | 10-1602580 | 3/2016 |

OTHER PUBLICATIONS

Hand, D. J., Statistics: A Very Short Introduction, Oxford University Press, p. 34-35 (Year: 2008).*

*Primary Examiner* — Robert A Cassity
(74) *Attorney, Agent, or Firm* — Lee & Morse, P.C.

(57) ABSTRACT

An inspection device includes a first processor, a second processor, and a server. The first processor detects first coordinates of first feature points from first images in a first image set. The second processor detects second coordinates of second feature points from second images in a second image set. The server generates reference coordinates based on the first coordinates and the second coordinates. The reference coordinates are transmitted to the first processor and the second processor. The first and second image sets correspond to scanned swaths on a wafer.

20 Claims, 12 Drawing Sheets

(51) Int. Cl.
*G03F 7/20* (2006.01)
*H01L 21/66* (2006.01)
*H01L 21/67* (2006.01)

(56) References Cited

U.S. PATENT DOCUMENTS

| | | |
|---|---|---|
| 7,106,895 B1 * | 9/2006 | Goldberg ............ G01N 21/9501 382/144 |
| 7,127,126 B2 | 10/2006 | Sakai et al. |
| 7,655,904 B2 | 2/2010 | Yamashita |
| 8,233,698 B2 | 7/2012 | Yamashita |
| 9,224,660 B2 | 12/2015 | Kulkarni et al. |
| 2003/0063190 A1 | 4/2003 | Young et al. |
| 2006/0193507 A1 * | 8/2006 | Sali .................... G01N 21/9501 382/145 |
| 2006/0265145 A1 * | 11/2006 | Huet ................. G01R 31/2846 702/35 |
| 2007/0133863 A1 | 6/2007 | Sakai et al. |
| 2007/0280527 A1 * | 12/2007 | Almogy .............. G03F 7/70491 382/149 |
| 2008/0259326 A1 * | 10/2008 | Kutscher ............ G01N 21/9501 382/144 |

* cited by examiner

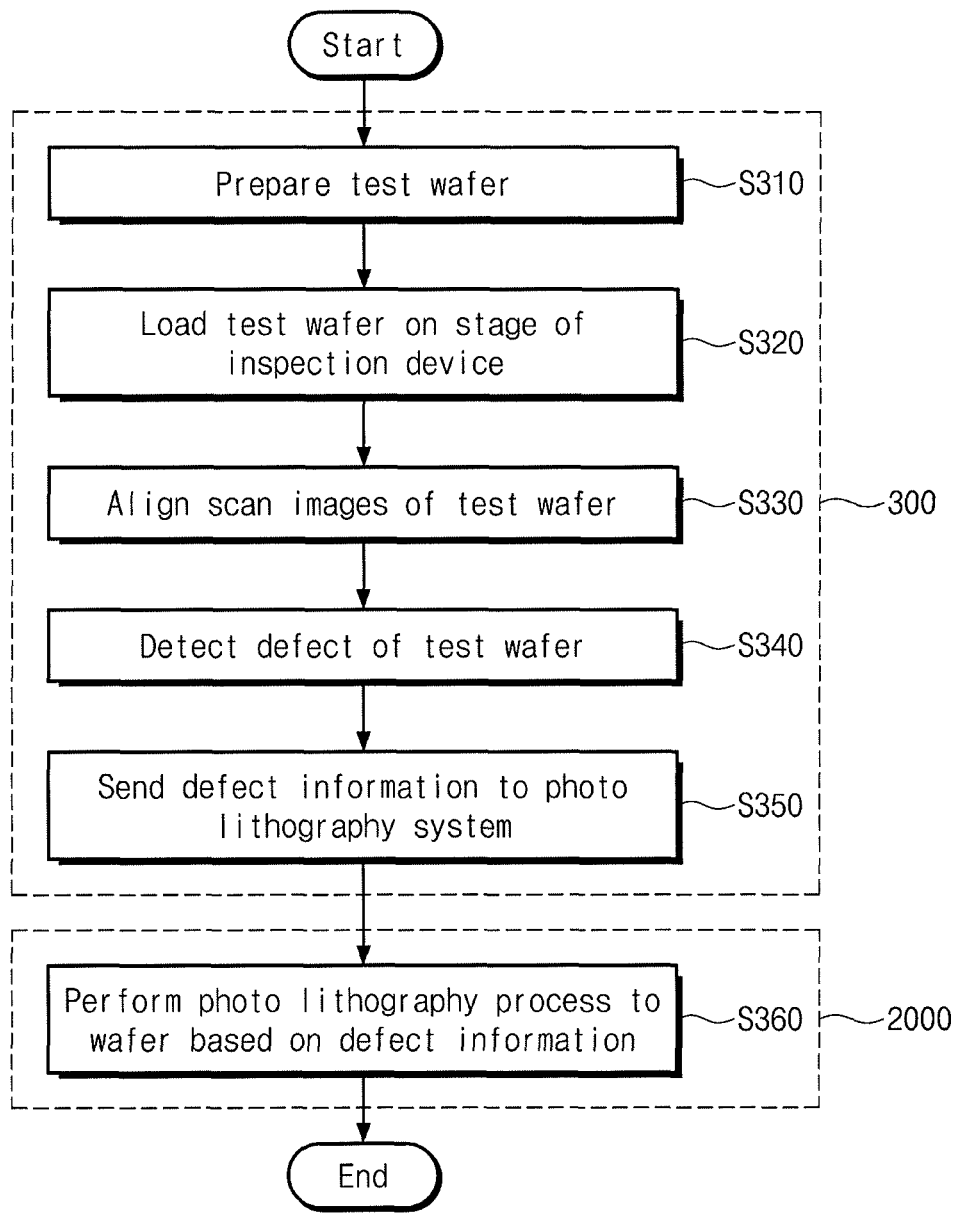

INSPECTION DEVICE FOR INSPECTING WAFER AND METHOD OF INSPECTING WAFER USING THE SAME

CROSS-REFERENCE TO RELATED APPLICATION

Korean Patent Application No. 10-2016-0160761, filed on Nov. 29, 2016, and entitled, "Inspection Device for Inspecting Wafer and Method of Inspecting Wafer Using the Same," is incorporated by reference herein in its entirety.

BACKGROUND

1. Field

One or more embodiments described herein relate to an inspection device for inspecting a wafer and a method for inspecting a wafer.

2. Description of the Related Art

A photolithography process may be used to print an integrated circuit layout on a wafer, and an inspection process may detect foreign substances, stains, scratches, or other defects on the wafer after the photolithography process. During inspection, the wafer should be aligned in order to allow an image sensor to capture proper images. If the wafer images are not aligned, the wafer may be determined to have defects which are actually not there.

SUMMARY

In accordance with one or more embodiments, an inspection device includes a first processor to detect first coordinates of first feature points from first images in a first image set among the plurality of image sets; a second processor to detect second coordinates of second feature points from second images in a second image set among the plurality of image sets; and a server to generate reference coordinates based on the first coordinates and the second coordinates and to transmit the reference coordinates to the first processor and the second processor, wherein the first and second image sets correspond to a same scanned swath on a wafer.

In accordance with one or more other embodiments, an inspection method includes receiving, from an image sensor, a plurality of image sets generated by scanning one inspection swath of a plurality of inspection swaths on a test wafer; detecting, by a first processor, first coordinates of first feature points from first images in a first image set among the plurality of image sets; detecting, by a second processor, second coordinates of second feature points from second images in a second image set among the plurality of image sets; generating, by the server, reference coordinates based on the first coordinates and the second coordinates; generating, by the first processor, first aligned images by aligning locations of the first coordinates to correspond to the reference coordinates based on the reference coordinates; and generating, by the second processor, second aligned images by aligning locations of the second coordinates to correspond to the reference coordinates based on the reference coordinates.

In accordance with one or more other embodiments, an apparatus includes first logic to detect coordinates of feature points from first images; second logic to detect coordinates of feature points from second images, the first and second images corresponding to a same scanned swath on a wafer; third logic to generate reference coordinates based on the coordinates of the feature points of the first and second images; and fourth logic to detect a defect of the wafer by comparing the first and second images based on the reference coordinates.

BRIEF DESCRIPTION OF THE DRAWINGS

Features will become apparent to those of skill in the art by describing in detail exemplary embodiments with reference to the attached drawings in which:

FIG. 13 illustrates an embodiment of a method for manufacturing a semiconductor device using a wafer inspection method.

DETAILED DESCRIPTION

Figure 1:
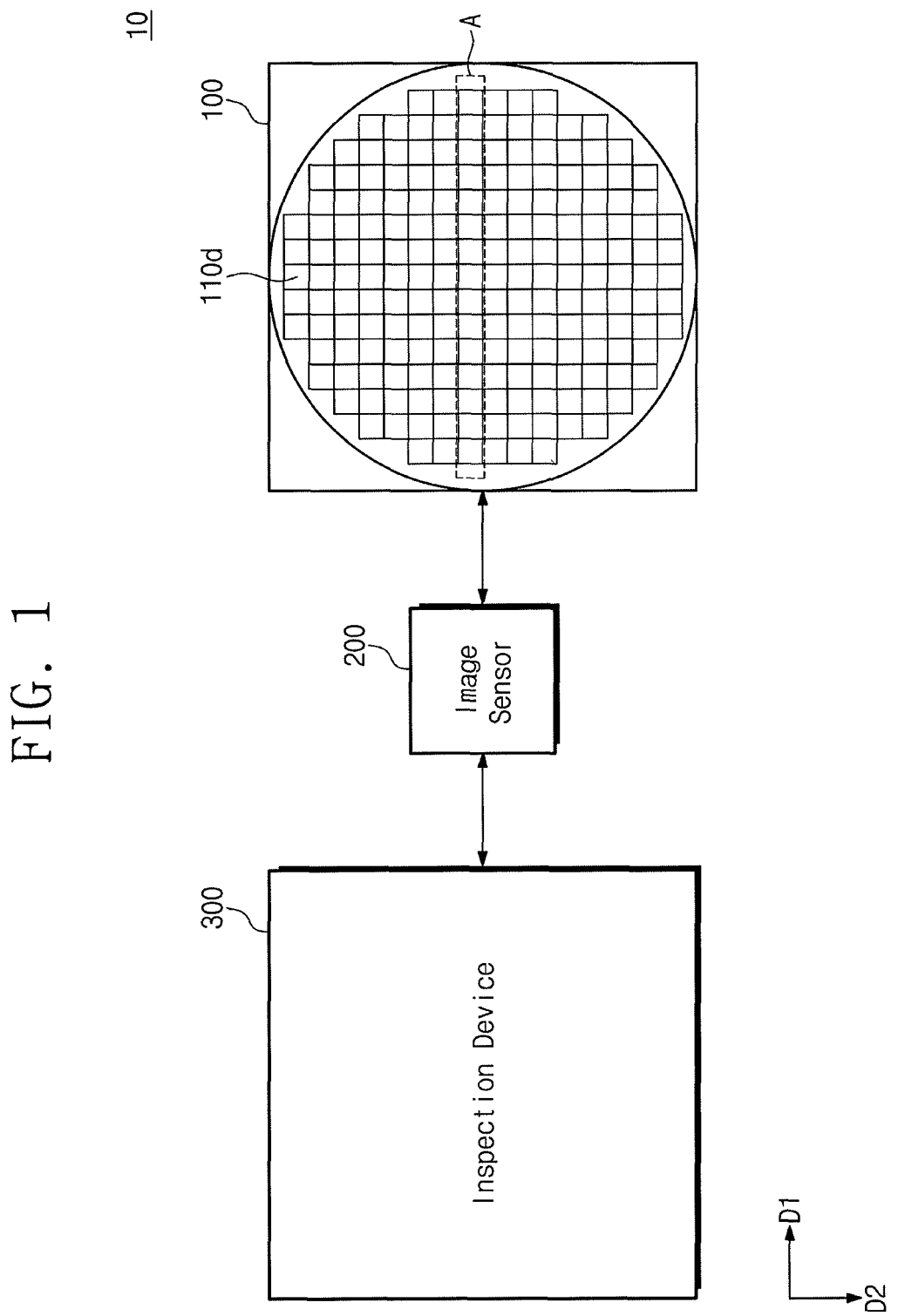
FIG. 1 illustrates an embodiment of a wafer inspection system.

FIG. 1 illustrates an embodiment of a wafer inspection system 10 which may include a wafer 100, an image sensor 200, and an inspection device 300. The wafer 100 may include a plurality of dies 110$d$. Each die 110$d$ may be, for example, a semiconductor chip and may include one or more pattern layouts. Each pattern layout may be designed to be the same or different.

The image sensor 200 may scan the wafer 100. A scan method of the image sensor 200 may be performed with reference to a first area A. The first area A may include a plurality of dies 110$d$ aligned in a first direction D1. The image sensor 200 may scan the first area A along the first direction D1. For example, the image sensor 200 may scan the dies 110$d$ in the first area A according to the first direction D1. The image sensor 200 may shoot (or capture an image of) the first area A several times while moving in a second direction D2. The image sensor 200 may scan the remaining dies 110$d$ using the method of scanning the first area A.

The image sensor 200 may generate images on patterns formed on the wafer 100 by scanning the wafer 100. The image sensor 200 may transmit the generated images to the inspection device 300. The image sensor 200 may shake due to one or more external influences. The image sensor 200 may not uniformly move in the first direction D1 or the second direction D2 because of the shaking. Thus, patterns in each image may not be uniform and may be shot in a different location.

The inspection device 300 may receive scanned images of the wafer 100 from the image sensor 200. The inspection device 300 may store and process the received images. The inspection device 300 may uniformly align patterns in the images. The inspection device 300 may check the degree of dislocation of patterns using feature points in the images and may align the remaining images based on feature points in a reference image.

Figure 2:
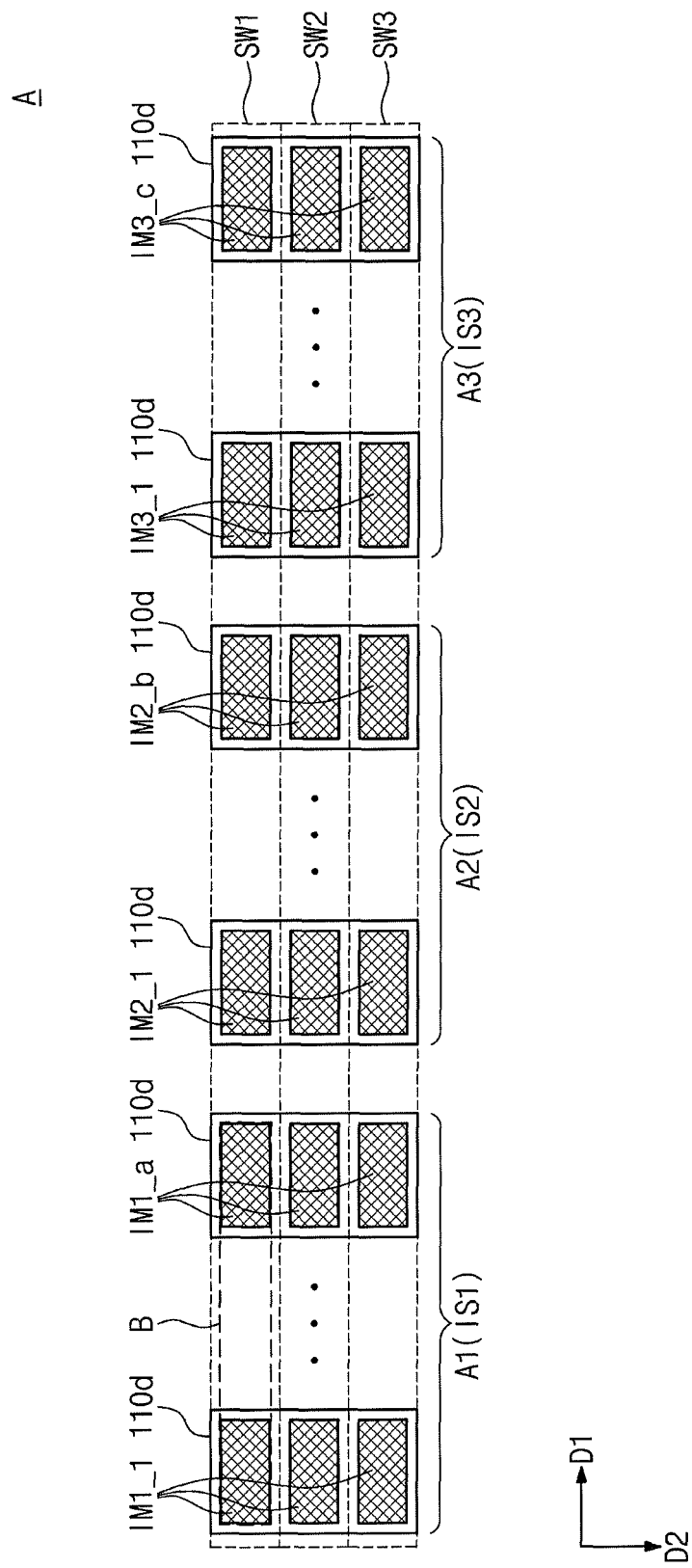
FIG. 2 illustrates an embodiment of a first area of a wafer.

FIG. 2 illustrates an embodiment of a first area of a wafer device of FIG. 1.

Referring to FIG. 2, the first area A may include a plurality of dies 110d. In the first area A, adjacent dies 110d may be defined as an area. For example, the first area A may include first through third sub areas A1, A2, and A3. The first through third sub areas A1, A2, and A3 may include the same number of dies 110d respectively. In one embodiment, the first area A may include a different number of (e.g., more or less than three) sub areas.

Referring to FIGS. 1 and 2, the image sensor 200 may scan the first area A based on a plurality of inspection swaths SW1, SW2, and SW3. The inspection swaths may be in a range where the image sensor 200 scans the first area A along the first direction D1. The image sensor 200 may scan the first inspection swath SW1 while moving along the first direction D1. When a scan of the first inspection swath SW1 is complete, the image sensor 200 moves along the second direction D2. The image sensor 200 may scan the second inspection swath SW2 while moving along the first direction D1. When a scan of the second inspection swath SW2 is complete, the image sensor 200 moves along the second direction D2. The image sensor 200 may scan the third inspection swath SW3 while moving along the first direction D1. When a scan of the second inspection swath SW2 is complete, an operation where the image sensor 200 scans the first area A may be complete. If an operation of scanning the first area A is finished, the image sensor 200 may scan another area of a lower portion of the first area A. FIG. 2 illustrates three inspection swathes SW1, SW2, and SW3. In one embodiment, the number of inspection swathes may be different from three.

The image sensor 200 may generate a plurality of image sets IS1, IS2, and IS3 from the one inspection swath. More specifically, to explain formation of the image sets, a case of scanning the first inspection swath SW1 of the image sensor 200 is explained as an example.

When the image sensor 200 scans the first inspection swath SW1, the image sensor 200 may generate first images IM1_1 to IM1_a shot in the first sub area A1 as a first image set IS1. The image sensor 200 may generate second images IM2_1 to IM2_b shot in the second sub area A2 as a second image set IS2. The image sensor 200 may generate third images IM3_1 to IM3_c shot in the third sub area A3 as a third image set IS3. The number of the first images IM1_1 to IM1_a, the number of the second images IM2_1 to IM2_b, and the number of the third images IM3_1 to IM3_c may be the same or different.

The image sensor 200 may transmit the first through third image sets IS1, IS2, and IS3 to the inspection device 300. When the first through third image sets IS1, IS2, and IS3 generated by shooting the first inspection swath SW1 are transmitted to the inspection device 300, the image sensor 200 may generate first through third image sets IS1, IS2, and IS3 in each of the second inspection swath SW2 and the third inspection swath SW3 in order.

Figure 3:
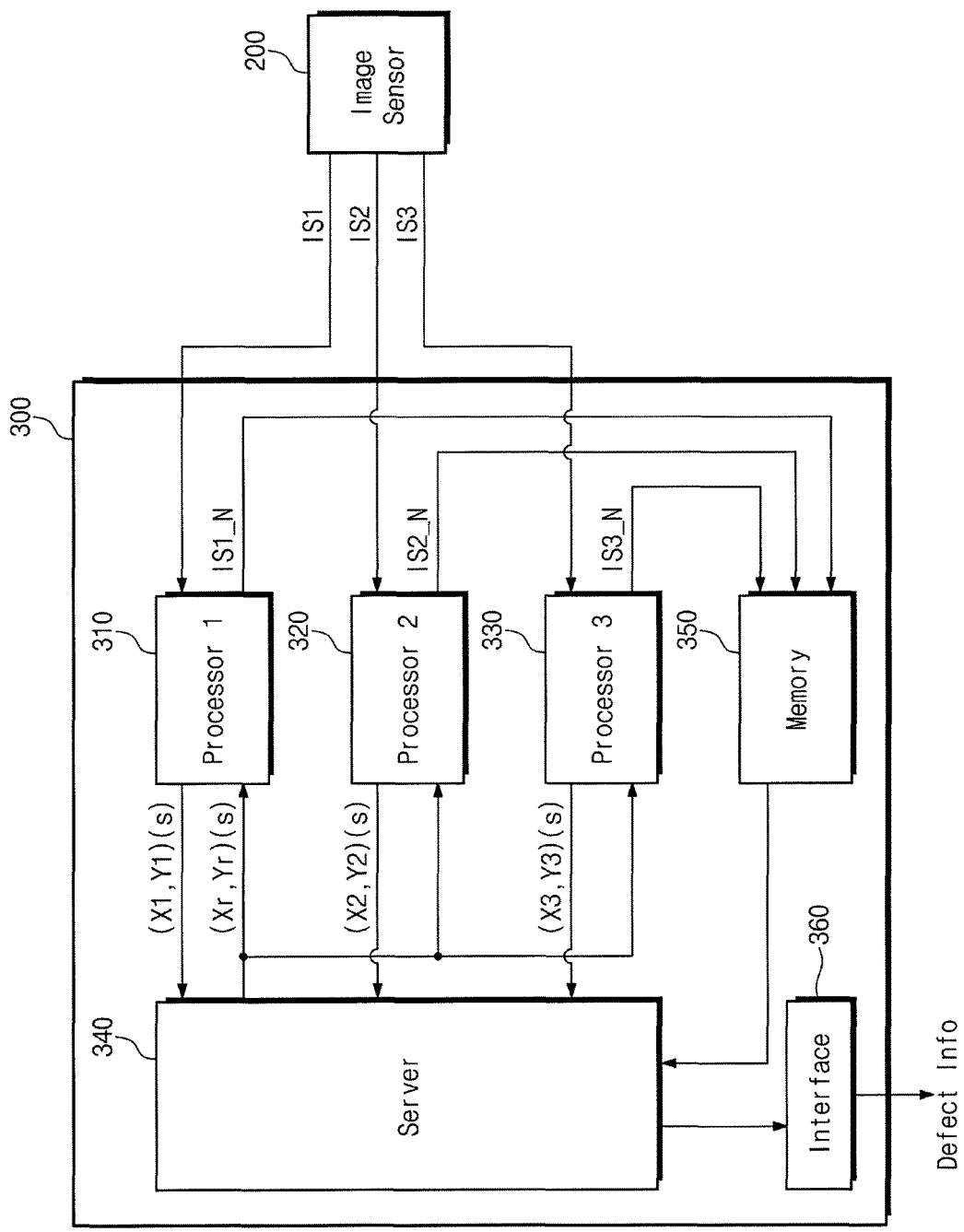
FIG. 3 illustrates an embodiment of an image sensor and an inspection device.

FIG. 3 illustrates an embodiment of an image sensor and an inspection device, which, for example, may correspond to those in FIG. 1. Referring to FIG. 3, the image sensor 200 may transmit the first through third image sets IS1, IS2, and IS3 to the inspection device 300. The inspection device 300 may include a first processor 310, a second processor 320, a third processor 330, a server 340, a memory 350, and an interface 360.

Each of the first through third processors 310, 320, and 330 may include at least one of a general-purpose processor or a special-purpose processor such as a workstation. Each of the first through third processors 310, 320, and 330 may perform various numerical operations and/or various logical operations. For example, each of the first through third processors 310, 320, and 330 may include at least one processor core, which, for example, may include a special purpose logic circuit (e.g., FPGA (field programmable gate array), ASICs (application specific integrated chips, etc.).

In one embodiment, the number of the processors may be the same as the number of received image sets, but this is not a necessity. The first through third image sets IS1, IS2, and IS3 may be generated from the image sensor 200. Thus, the inspection device 300 may include the first through third processors 310, 320, and 330. The number of the processors may be different from three in one embodiment.

The first processor 310 may receive the first image set IS1. The first processor 310 may extract one or more feature points of each of the first images IM1_1 to IM1_a in the first image set IS1. The first processor 310 may calculate a moving path of the image sensor 200 while the first image set IS1 is shot based on first coordinates (X1, Y1)(s) of the feature points.

Figure 4:
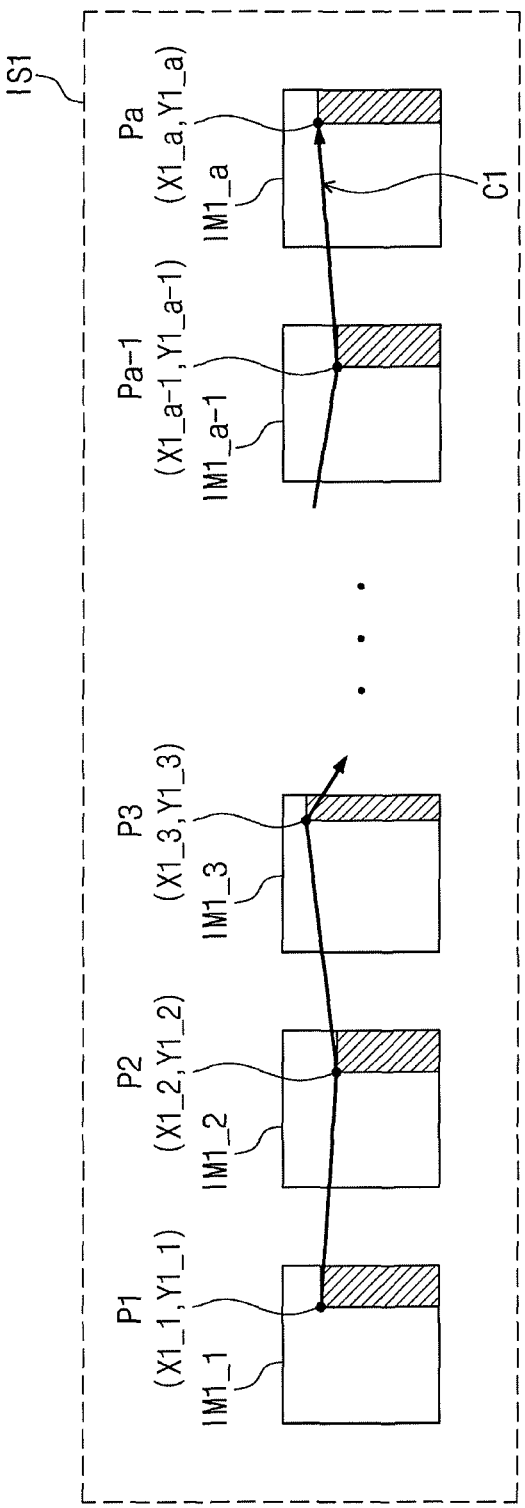
FIG. 4 illustrates an example of a moving path of an image sensor for capturing a first image set.

FIG. 4 illustrates an example of a moving path of an image sensor while shooting a first image set of FIG. 3. Referring to FIGS. 3 and 4, the first processor 310 may extract first feature points P1 to Pa from the first images IM1_1 to IM1_a of the first image set IS1. Referring to FIGS. 2 and 4, the first feature points P1 to Pa may be set based on the same location on the dies 110d in the first sub area A1. However, when the image sensor 200 cannot scan the first inspection swath SW1 uniformly, the first feature points P1 to Pa may be scanned at different locations in the first images IM1_1 to IM1_a.

A moving path of the image sensor 200 may be calculated based on first coordinates (X1_1, Y1_1) to (X1_a, Y1_a) of the first feature points P1 to Pa. For example, the image sensor 200 may move to a first path C1 while scanning the first image set IS1. The first processor 310 may provide information about the first coordinates (X1, Y1)(s) (e.g., (X1_1, Y1_1) to (X1_a, Y1_a)) to the server 340.

The second processor 320 may receive the second image set IS2. The second processor 320 may extract one or more feature points from the second images IM2_1 to IM2_a in the second image set IS2. The second processor 320 may calculate a moving path of the image sensor 200 while the second image set IS2 is shot based on second coordinates (X2, Y2)(s) of the features points.

Figure 5:
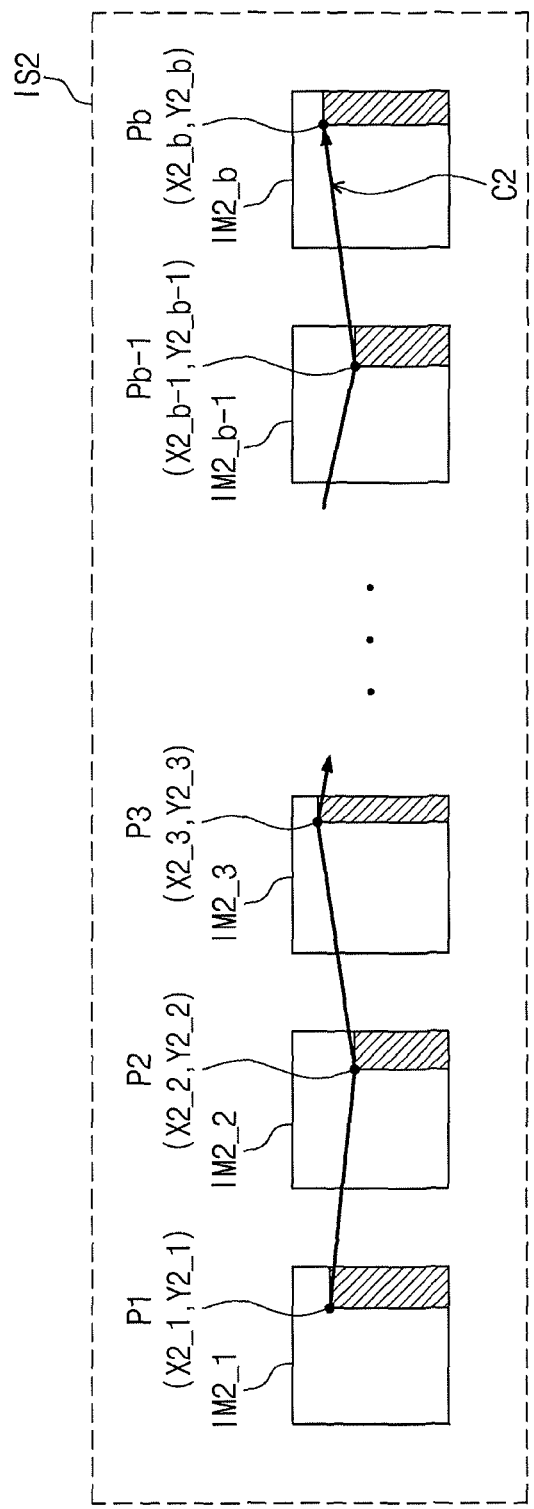
FIG. 5 illustrates an example of a moving path of an image sensor for capturing a second image set.

FIG. 5 illustrates an example of a moving path of an image sensor while shooting a second image set of FIG. 3. Referring to FIGS. 3 and 5, the second processor 320 may extract second feature points P1 to Pb from the second images IM2_1 to IM2_b of the second image set IS2. Referring to FIGS. 2 and 5, the second feature points P1 to Pb may be set based on the same location on the dies 110d in the second sub area A2.

However, when the image sensor 200 cannot scan the first inspection swath SW1 uniformly, the second feature points P1 to Pb may be scanned at different locations in the second images IM2_1 to IM2_b. A moving path of the image sensor 200 may be calculated based on second coordinates (X2_1, Y2_1) to (X2_b, Y2_b) of the second feature points P1 to Pb. For example, the image sensor 200 may move to a second path C2 while scanning the second image set IS2. The second processor 320 may provide information about the second coordinates (X2, Y2)(s) (e.g., (X2_1, Y2_1) to (X2_b, Y2_b)) to the server 340.

The third processor 330 may receive the third image set IS3. The third processor 330 may extract one or more feature points of each of the third images IM3_1 to IM3_c in the third image set IS3. The third processor 330 may calculate a moving path of the image sensor 200 while the third image set IS3 is shot based on third coordinates (X3, Y3)(s) of the features points.

Figure 6:
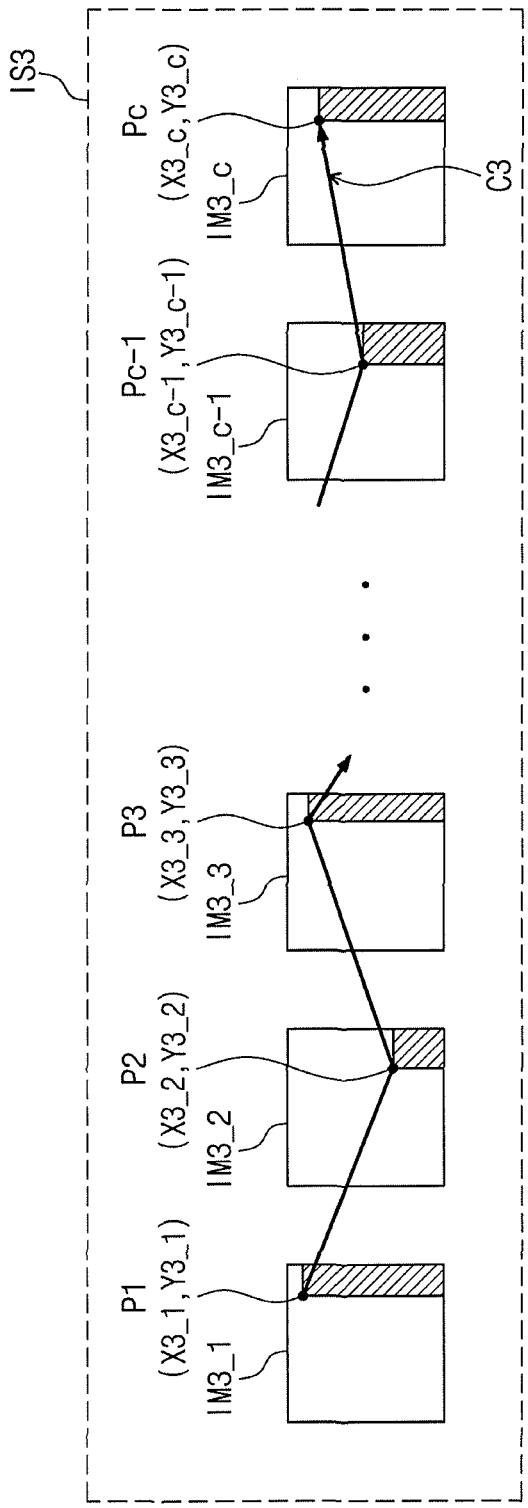
FIG. 6 illustrates an example of a moving path of an image sensor for capturing a third image set.

FIG. 6 illustrates an embodiment of a moving path of an image sensor while shooting a third image set of FIG. 3. Referring to FIGS. 3 and 6, the third processor 330 may extract third feature points P1 to Pc from the third images IM3_1 to IM3_c of the second image set IS2. Referring to FIGS. 2 and 6, the third feature points P1 to Pc may be set based on the same location on the dies 110d in the second sub area A2.

However, when the image sensor 200 cannot scan the first inspection swath SW1 uniformly, the third feature points P1 to Pc may be scanned at different locations in the third images IM3_1 to IM3_c. A moving path of the image sensor 200 may be calculated based on third coordinates (X3_1, Y3_1) to (X3_c, Y3_c) of the third feature points P1 to Pc. For example, the image sensor 200 may move to a third path C3 while scanning the third image set IS3. The third processor 330 may provide information about the third coordinates (X3, Y3)(s) (e.g., (X3_1, Y3_1) to (X3_c, Y3_c)) to the server 340.

The server 340 may receive the first coordinates (X1, Y1)(s) from the first processor 310 and may receive the second coordinates (X2, Y2)(s) from the second processor 320. The server 340 may receive the third coordinates (X3, Y3)(s) from the third processor 330. The server 340 may calculate reference coordinates (Xr, Yr)(s) based on the first coordinates (X1, Y1)(s), the second coordinates (X2, Y2)(s), and the third coordinates (X3, Y3)(s).

The server 340 may calculate a first reference X coordinate (Xr_1) using first X coordinates (X1_1, X2_1. X3_1) of the first coordinates (X1, Y1)(s), the second coordinates (X2, Y2)(s), and the third coordinates (X3, Y3)(s). The server 340 may calculate a first reference Y coordinate (Yr_1) using first Y coordinates (Y1_1, Y2_1, Y3_1) of the first coordinates (X1, Y1)(s), the second coordinates (X2, Y2)(s), and the third coordinates (X3, Y3)(s). The first reference X coordinate (Xr_1) and the first reference Y coordinate (Yr_1) are a pair of first reference coordinate (Xr_1, Yr_1).

The first reference coordinate (Xr_1, Yr_1) may be calculated, for example, based on an average value of the first X coordinates (X1_1, X2_1, X3_1) and an average value of the first Y coordinates (Y1_1, Y2_1, Y3_1). The first reference coordinate (Xr_1, Yr_1) may also be calculated based on a median value of the first X coordinates (X1_1, X2_1, X3_1) and a median value of the first Y coordinates (Y1_1, Y2_1, Y3_1). As described above, the server 340 may calculate the reference coordinates (Xr, Yr)(s) and transmit the calculated reference coordinates (Xr, Yr)(s) to the first through third processors 310, 320, and 330.

The first processor 310 may receive the reference coordinates (Xr, Yr)(s). The first processor 310 may align locations of the first coordinates (X1, Y1)(s) based on the reference coordinates (Xr, Yr)(s).

Figure 7:
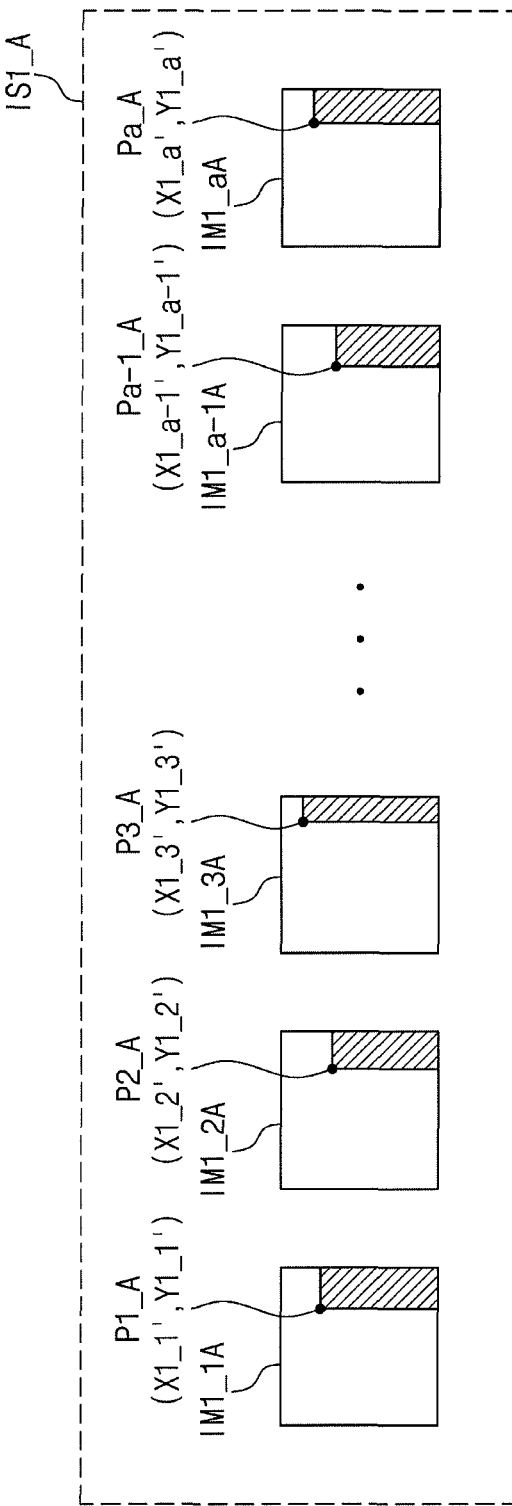
FIG. 7 illustrates an embodiment of a method for generating a first image set aligned in a first processor.

FIG. 7 illustrates an embodiment of a method for generating a first image set aligned in a first processor of FIG. 1. Referring to FIGS. 3, 4, and 7, the first processor 310 may align locations of the first coordinates (X1, Y1)(s) based on the reference coordinates (Xr, Yr)(s). For example, the first processor 310 may align locations of the remaining coordinates of the first images IM1_1 to IM1_a as much as locations of the first coordinates (X1, Y1)(s) are aligned. The first processor 310 may generate a first aligned image set IS1_A.

The first aligned image set IS1_A may include first aligned images IM1_1A to IM1_aA. The first aligned images IM1_1A to IM1_aA may include first aligned feature points P1_A to Pa_A respectively. The first aligned feature points P1_A to Pa_A may have first aligned coordinates (X1_1's, Y1_1') to (X1_a', Y1_a') respectively. Locations of the first aligned coordinates (X1_1', Y1_1') to (X1_a', Y1_a') may be the same as locations of the reference coordinates (Xr, Yr)(s).

Referring back to FIG. 3, the second processor 320 may align locations of the second coordinates (X2, Y2)(s) based on the reference coordinates (Xr, Yr)(s).

Figure 8:
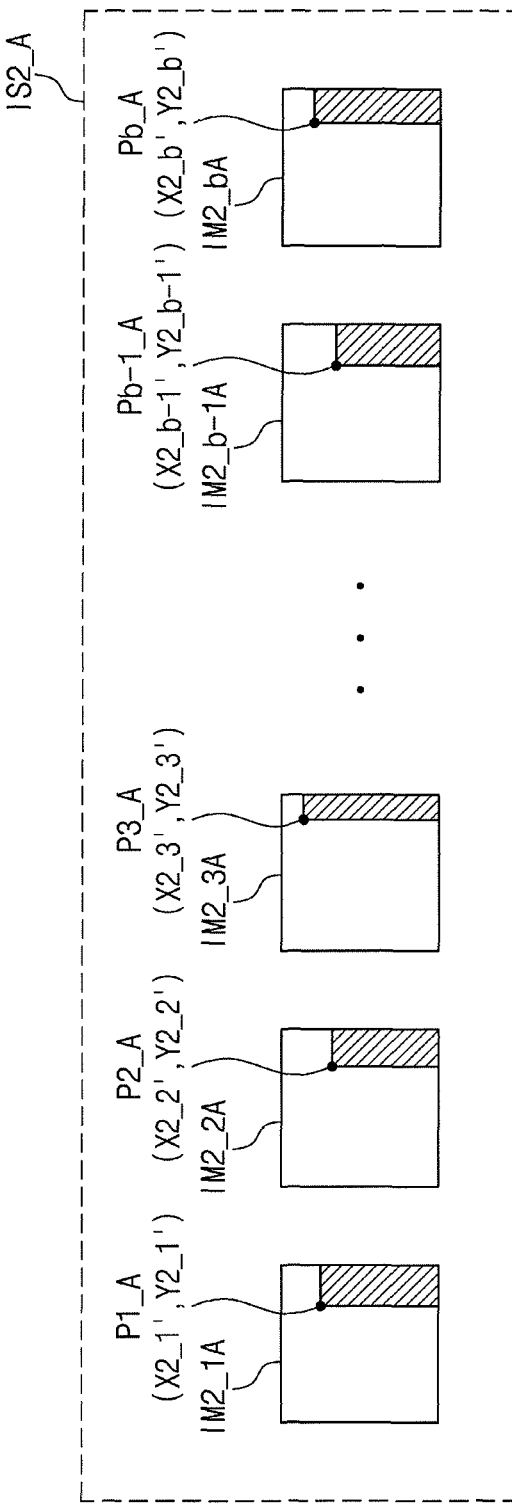
FIG. 8 illustrates an embodiment of a method for generating a second image set aligned in a second processor.

FIG. 8 illustrates an embodiment of a method for generating a second image set aligned in a second processor of FIG. 1. Referring to FIGS. 3, 4, and 8, the second processor 320 may align locations of the second coordinates (X2, Y2)(s) based on the reference coordinates (Xr, Yr)(s). For example, the second processor 320 may align locations of the remaining coordinates of the second images (IM2_1 to IM2_b) as much as locations of the second coordinates (X2, Y2)(s) are aligned. The second processor 320 may generate a second aligned image set IS2_A.

The second aligned image set IS2_A may include second aligned images IM2_1A to IM2_bA. The second aligned images IM2_1A to IM2_bA may include second aligned feature points P1_A to Pb_A respectively. The second aligned feature points P1_A to Pb_A may have second aligned coordinates (X2_1', Y2_1') to (X2_b', Y2_b') respectively. Locations of the second aligned coordinates (X2_1 Y2_1') to (X2_b', Y2_b') may be the same as locations of the reference coordinates (Xr, Yr)(s).

Referring back to FIG. 3, the third processor 330 may align locations of the third coordinates (X3, Y3)(s) based on the reference coordinates (Xr, Yr)(s).

Figure 9:
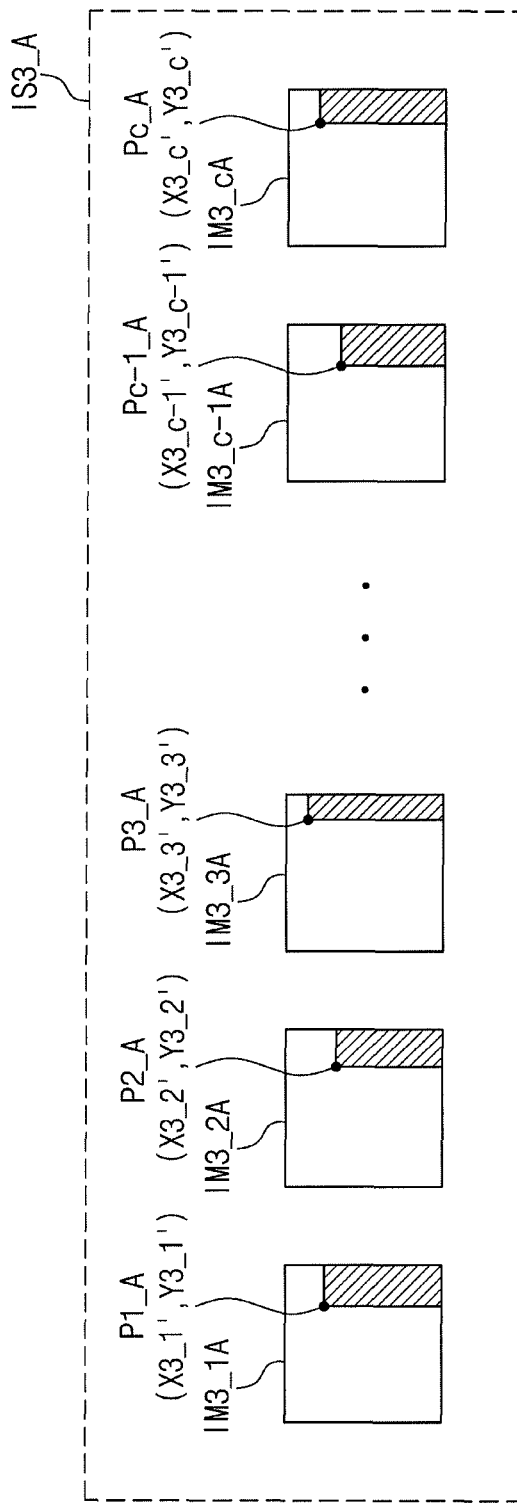
FIG. 9 illustrates an embodiment of a method for generating a third image set aligned in a third processor.

FIG. 9 illustrates a method for generating a third image set aligned in a third processor of FIG. 1. Referring to FIGS. 3, 4, and 9, the third processor 330 may align locations of the third coordinates (X3, Y3)(s) based on the reference coordinates (Xr, Yr)(s). For example, the third processor 330 may align locations of the remaining coordinates of the third images IM3_1 to IM3_c as much as locations of the third coordinates (X3, Y3)(s) are aligned. The third processor 330 may generate a third aligned image set IS3_A.

The third aligned image set IS3_A may include third aligned images IM3_1A to IM3_cA. The third aligned images IM3_1A to IM3_cA may include third aligned feature points P1_A to Pc_A respectively. The third aligned feature points P1_A to Pc_A may have third aligned coordinates (X3_1', Y3_1') to (X3_c', Y3_c') respectively. Locations of the third aligned coordinates (X3_1', Y3_1') to (X3_c', Y3_c') may be the same as locations of the reference coordinates (Xr, Yr)(s).

Referring back to FIG. 3, the first processor 310 may designate one of the first aligned images IM1_1A to IM1_aA as a reference image and may designate the remaining images (except the reference image) as target images. The first processor 310 may align the location of each of the target images based on the reference image. For example, the first processor 310 may align the location of each of coordinates of the target images based on locations of coordinates of the reference image. The reference image and the aligned target images may be defined as a new first image set IS1_N. The first processor 310 may transmit the new first image set IS1_N to the memory 350.

The second processor 320 may designate one of the second aligned images IM2_1 A to IM2_bA as a reference image and may designate the remaining images (except the reference image) as target images. The second processor 320 may align the location of each of the target images based on the reference image. For example, the second processor 320 may align the location of each of coordinates of the target images based on locations of coordinates of the reference image. The reference image and the aligned target images may be defined as a new second image set IS2_N. The second processor 320 may transmit the new second image set IS2_N to the memory 350.

The third processor 330 may designate one of the third images aligned IM3_1A to IM3_cA as a reference image and may designate the remaining images (except the reference image) as target images. The third processor 330 may align the location of each of the target images based on the reference image. For example, the third processor 330 may align the location of each of coordinates of the target images based on locations of coordinates of the reference image. The reference image and the aligned target images may be defined as a new third image set IS3_N. The third processor 330 may transmit the new third image set IS3_N to the memory 350. The first through third processors 310, 320, and 330 may repeat those aforementioned operations until all images on the wafer 100 are received.

The memory 350 may receive new first through third image sets IS1_N, IS2_N, and IS3_N from the first through third processors 310, 320, and 330 respectively. The memory 350 may be implemented by a volatile memory device or a nonvolatile memory device. A volatile memory device loses its stored data when power is interrupted. Examples of the volatile memory device are a static RAM (SRAM), a dynamic RAM (DRAM), a synchronous DRAM, etc. A nonvolatile memory device retains its stored data even when a power supply is interrupted. Examples of the nonvolatile memory device are a read only memory (ROM), a programmable ROM (PROM), an electrically programmable ROM (EPROM), an electrically erasable and programmable ROM (EEPROM), a flash memory device, a phase change RAM (PRAM), a magnetic RAM (MRAM), a resistive RAM (RRAM), and a ferroelectric RAM (FRAM).

The memory 350 may transmit the new first through third image sets IS1_N, IS2_N, and IS3_N on the first inspection swath SW1 to the server 340 based on a request of the sever 340. When a scan on all the dies 100d of the wafer 100 is completed, the memory 350 may transmit new image sets to the server 340.

The server 340 may compare new first through third images with one another in the new first through third image sets IS1_N, IS2_N, and IS3_N, respectively. The server 340 may detect defects in the wafer 100 by comparing the new first through third images. The server 340 may transmit information about the defects in the wafer 100 to the interface 360.

The interface 360 may output the information about the defects in the wafer 100 to a source external to the inspection device 300. For example, the interface 360 may transmit the information about the defects in the wafer 100 to a user of the inspection device 300. The interface 360 may also provide the information about the defects in the wafer 100 to a photolithography system. The photolithography system may change an exposure condition or a focus condition based on the information about the defects in the wafer 100.

An inspection device receives scan images on a wafer from an image sensor and aligns the received scan images. For example, the inspection device designates a reference image among the scan images and aligns target images based on the reference image. However, if the image sensor is shaken during scanning of the wafer, the location of a pattern in the scan images may be different from the location that actually exists on a die. Because of this, the inspection device may not obtain an accurate image on the wafer even though the scan images are aligned.

To obtain an accurate image on the wafer, the inspection device 300 according to example embodiments may detect the first coordinates (X1, Y1)(s) on the first feature points P1 to Pa of the first image set IS1, the second coordinates (X2, Y2)(s) on the second feature points P1 to Pb of the second image set IS2, and the third coordinates (X3, Y3)(s) on the third feature points P1 to Pc of the third image set IS3.

Locations of the first coordinates (X1, Y1)(s), the second coordinates (X2, Y2)(s), and the third coordinates (X3, Y3)(s) are different from one another. Thus, when the first image set IS1, the second image set IS2, and the third image set IS3 are aligned based on the first coordinates (X1, Y1)(s), the second coordinates (X2, Y2)(s), and the third coordinates (X3, Y3)(s) respectively, the first image set IS1, the second image set IS2, and the third image set IS3 may be aligned based on different criteria.

To accurately align the first image set IS1, the second image set IS2, and the third image set IS3, the inspection device 300 may calculate the reference coordinates (Xr, Yr)(s) based on the first coordinates (X1, Y1)(s), the second coordinates (X2, Y2)(s), and the third coordinates (X3, Y3)(s). The inspection device 300 may align the first images IM1_1 to IM1_a of the first image set IS1, the second images IM2_1 to IM2_b of the second image set IS2, and the third images IM3_1 to IM3_c of the third image set IS3 based on the locations of the reference coordinates (Xr, Yr)(s). Using the same manner, the inspection device 300 may compensate shaking of the image sensor 200 and may accurately align images on the wafer 100.

Figure 10:
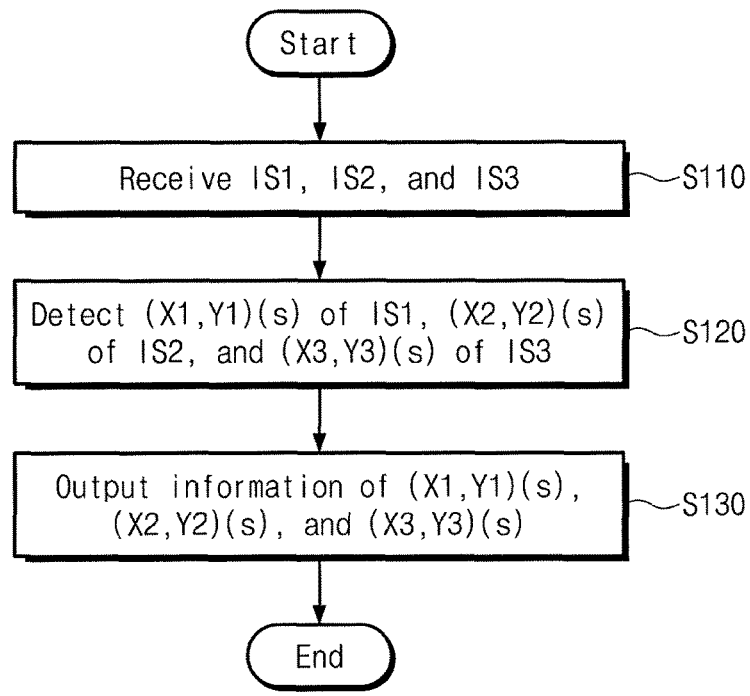
FIG. 10 illustrates an embodiment of a method for operating an inspection device.

FIG. 10 illustrates an embodiment of a method for operating an inspection device of FIG. 3. Referring to FIG. 10, in operation S110, the inspection device 300 may receive the first image set IS1, the second image set IS2, and the third image set IS3. The first image set IS1 includes the first images IM1_1 to IM1_a. The second image set IS2 includes the second images IM2_1 to IM2_b. The third image set IS3 includes the third images IM3_1 to IM3_c. The number of the first images IM1_1 to IM1_a, the number of the second images IM2_1 to IM2_b, and the number of the third images IM3_1 to IM3_c may be the same or different.

In operation S120, the first processor 310 of the inspection device 300 may detect the first coordinates (X1, Y1) (s) in the first image set IS1. The second processor 320 of the inspection device 300 may detect the second coordinates (X2, Y2) (s) in the second image set IS2. The third processor 330 of the inspection device 300 may detect the third coordinates (X3, Y3) (s) in the third image set IS3. The first coordinates (X1, Y1)(s) are locations of the first feature points P1 to Pa of the first images IM1_1 to IM1_a. The second coordinates (X2, Y2)(s) are locations of the second feature points P1 to Pb of the second images IM2_1 to IM2_b. The third coordinates (X3, Y3)(s) are locations of the third feature points P1 to Pc of the third images IM3_1 to IM3_c.

In operation S130, the first processor 310 of the inspection device 300 outputs the first coordinates (X1, Y1)(s) to the server 340. The second processor 320 of the inspection device 300 outputs the second coordinates (X2, Y2)(s) to the server 340. The third processor 330 of the inspection device 300 outputs the third coordinates (X3, Y3)(s) to the server 340.

Figure 11:
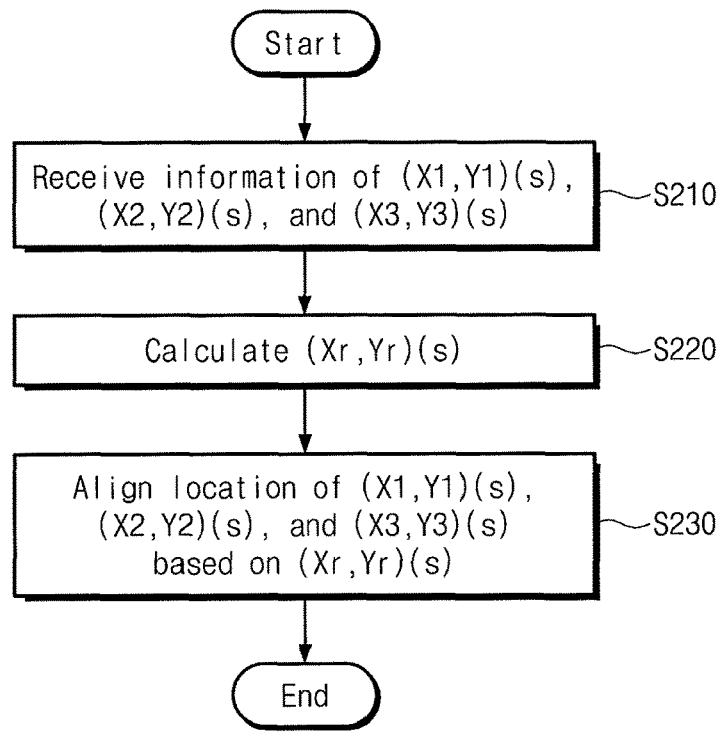
FIG. 11 illustrates an embodiment of a method for calculating reference coordinates of an inspection device.

FIG. 11 illustrates an embodiment of a method for calculating reference coordinates of an inspection device of FIG. 3. Referring to FIGS. 3, 10, and 11, in operation S210, the server 340 of the inspection device 300 receives the first coordinates (X1, Y1)(s), the second coordinates (X2, Y2)(s), and the third coordinates (X3, Y3)(s).

In operation S220, the server 340 of the inspection device 300 calculates the reference coordinates (Xr, Yr)(s) based on the first coordinates (X1, Y1)(s), the second coordinates (X2, Y2)(s), and the third coordinates (X3, Y3)(s). For example, the server 340 of the inspection device 300 calculates the reference coordinates (Xr, Yr)(s) using average values of the first coordinates (X1, Y1)(s), the second coordinates (X2, Y2)(s), and the third coordinates (X3, Y3)(s). The server 340 of the inspection device 300 calculates the reference coordinates (Xr, Yr)(s) using median values of the second coordinates (X2, Y2)(s) and the third coordinates (X3, Y3)(s). The server 340 of the inspection device 300 may transmit the reference coordinates (Xr, Yr)(s) to the first through third processors 310, 320, and 330.

In operation S230, the first processor 310 of the inspection device 300 may align locations of the first coordinates (X1, Y1)(s) based on the reference coordinates (Xr, Yr)(s). The second processor 320 of the inspection device 300 may align locations of the second coordinates (X2, Y2)(s) based on the reference coordinates (Xr, Yr)(s). The third processor 330 of the inspection device 300 may align locations of the third coordinates (X3, Y3)(s) based on the reference coordinates (Xr, Yr)(s). Using the method described with reference to FIG. 11, the inspection device 300 may compensate shaking of the image sensor 200 in each of the first image set IS1, the second image set IS2, and the third image set IS3.

Figure 12:
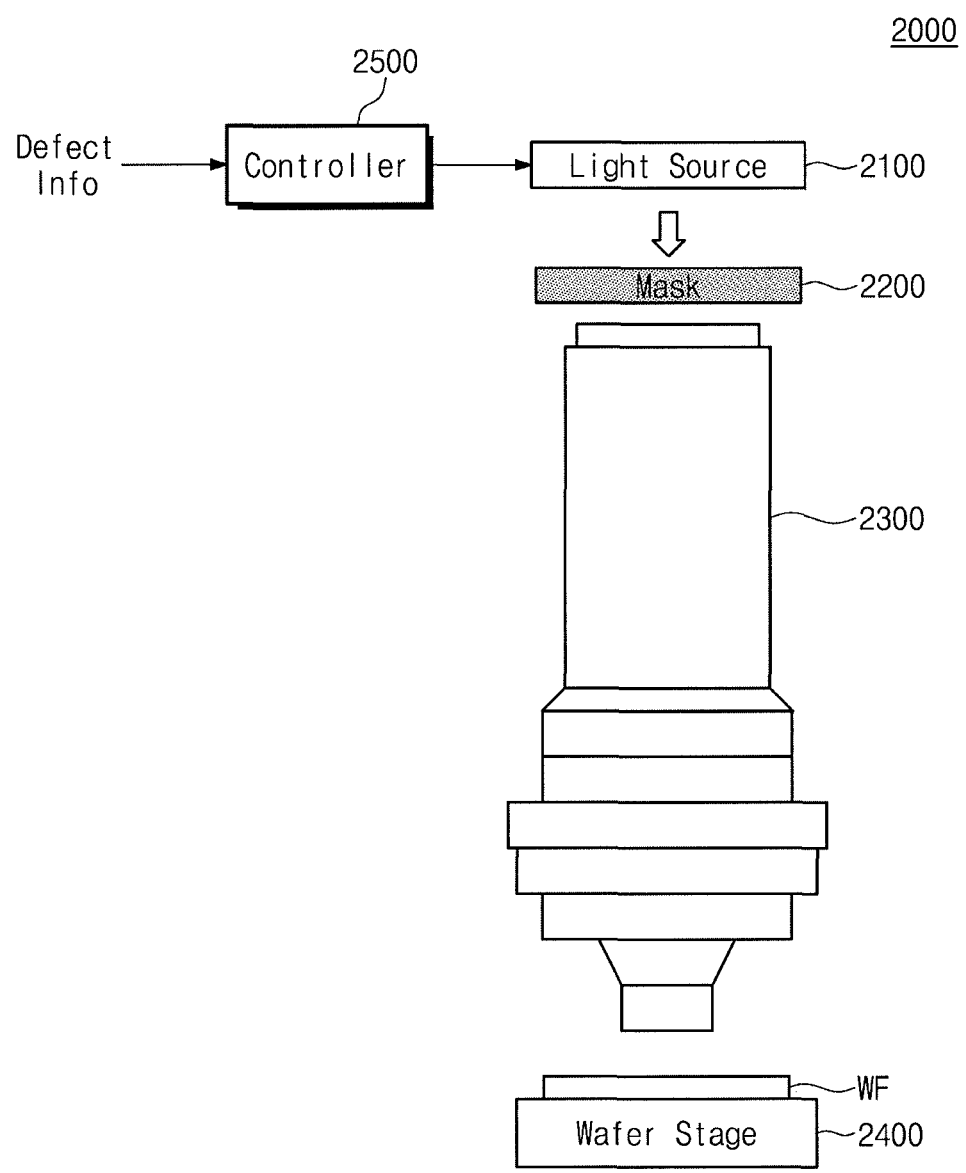
FIG. 12 illustrates an embodiment of a photolithography system for performing a photolithography operation on a wafer.

FIG. 12 illustrates an embodiment of a photolithography system 2000 for performing a photolithography operation on a wafer. Referring to FIG. 12, the photolithography system 2000 may include a light source 2100, a mask 2200, a reduction projection device 2300, a wafer stage 2400, and a controller 2500. The photolithography system 2000 may include a number of additional features, e.g., a sensor used to measure the height and slope of a surface of a wafer WF.

The light source 2100 may emit light. Light emitted by the light source 2100 may be irradiated into the mask 2200. The light source 2100 may include an ultraviolet light source, e.g., a KrF light source having a wavelength of 234 nm or a KrF light source having a wavelength of 193 nm.

The light source 2100 may further include a collimator to convert ultraviolet light to parallel light. The parallel light may be provided to the mask 2200. For example, the collimator may include a dipole aperture or a quadruple aperture to control the depth of focus of ultraviolet light. An exposure condition or a focus condition of the light source 2100 may be changed by the controller 2500.

The mask 2200 may include image patterns for use in printing a layout pattern on the wafer WF. The image patterns may include, for example, a transparent area and an opaque area. The transparent area may be formed, for example, by etching a metal layer on the mask 2200. The transparent area may transmit light emitted by the light source 2100. Light may not penetrate the opaque area.

The reduction projection device 2300 may receive light that passed through the transparent area of the mask 2200. The reduction projection device 2300 may match circuit patterns of the layout to be printed on the wafer WF with the image patterns of the mask 2200. The wafer stage 2400 may support the wafer WF.

The controller 2500 may receive defect information from the inspection device of FIG. 3. The controller 2500 may change an exposure condition or a focus condition of the photolithography system 2000 based on the defect information. For example, the controller 2500 may change an exposure condition or a focus condition to reduce or eliminate the occurrence of defects on the wafer WF.

The transparent area in the image patterns of the mask 2200 may transmit light emitted by the light source 2100. Light that has passed through the mask 2200 may be irradiated into the wafer WF through the reduction projection device 2300. As a result, a layout pattern including one or more circuit patterns corresponding to the image patterns of the mask 2200 may be printed on the wafer WF.

As integration of a semiconductor process increases, the distance between image patterns of the mask 2200 may reduce and the width of the transparent area may reduced. Because of this "proximity," interference and diffraction of light may occur and a distorted layout different from a desired layout may be printed on the wafer WF. When the distorted layout is printed on the wafer WF, the circuits on the wafer WF may not operate correctly.

To prevent distortion of the layout, a resolution enhancement technology is used. Optical proximity correction is an example of the resolution enhancement technology. According to optical proximity correction, the degree of distortion (such as interference and diffraction) of light may be predicted. Image patterns to be formed on the mask 2200 may be biased in advance based on the predicted result. As a result, a correct and desired layout pattern may be printed on the wafer.

FIG. 13 illustrates an embodiment of a method for manufacturing a semiconductor device using a wafer inspection method. Referring to FIGS. 1, 12 and 13, in operation S310, a test wafer (e.g., wafer 100 of FIG. 1) may be prepared. The test wafer 100 may include dies 110d, which include pattern layouts which may or may not be the same.

In operation S320, the test wafer 100 may be loaded on a stage.

In operation S330, the inspection device 300 may align scan images (e.g., IM1_1 to IM1_a, IM2_1 to IM2_b, IM3_1 to IM3_c) of the test wafer 100. The inspection device 300 may align scan images, for example, as described with reference to FIGS. 3 through 10.

In operation S340, the inspection device 300 may detect defects on the test wafer 100 based on the aligned scan images.

In operation S350, the inspection device 300 may transmit defect information to the photolithography system 2000. The operations S310 to S350 may be performed in the inspection device 300.

In operation S360, the photolithography system 2000 may perform a photolithography process on the wafer WF. The photolithography system 2000 may change an exposure condition and a focus condition based on the defect information to irradiate light into the wafer WF.

The methods, processes, and/or operations described herein may be performed by code or instructions to be executed by a computer, processor, controller, or other signal processing device. The computer, processor, controller, or other signal processing device may be those described herein or one in addition to the elements described herein. Because the algorithms that form the basis of the methods (or operations of the computer, processor, controller, or other signal processing device) are described in detail, the code or instructions for implementing the operations of the method embodiments may transform the computer, processor, controller, or other signal processing device into a special-purpose processor for performing the methods described herein.

The processors, controllers, servers, interfaces, and other signal and image processing and signal and image generating features of the disclosed embodiments may be implemented in logic which, for example, may include hardware, software, or both. When implemented at least partially in hardware, the processors, controllers, servers, interfaces, and other signal and image processing and signal and image generating features may be, for example, any one of a variety of integrated circuits including but not limited to an application-specific integrated circuit, a field-programmable gate array, a combination of logic gates, a system-on-chip, a microprocessor, or another type of processing or control circuit.

When implemented in at least partially in software, the processors, controllers, servers, interfaces, and other signal and image processing and signal and image generating features may include, for example, a memory or other storage device for storing code or instructions to be executed, for example, by a computer, processor, microprocessor, controller, or other signal processing device. The computer, processor, microprocessor, controller, or other signal processing device may be those described herein or one in addition to the elements described herein. Because the algorithms that form the basis of the methods (or operations of the computer, processor, microprocessor, controller, or other signal processing device) are described in detail, the code or instructions for implementing the operations of the method embodiments may transform the computer, processor, controller, or other signal processing device into a special-purpose processor for performing the methods described herein.

In accordance with one or more example embodiments, defects that occur in a test wafer based on photolithography conditions may be easily detected using the wafer test method and the wafer test system. Based on information relating to defects that occur based on photolithography conditions, required photolithography conditions (e.g., ones that reduce or minimize the occurrence of defects) from photolithography conditions split on the test wafer may be selected. Defects that may occur on the wafer may be reduced or minimized by performing a photolithography process on a wafer for forming a semiconductor integrated circuit on one or more selected photolithography conditions. Thus, a method for manufacturing a semiconductor device that may reduce or minimize occurrence of defects may be provided. According to example embodiments, the accuracy of detecting defects on a wafer may be improved by aligning images formed by scanning a wafer using reference coordinates.

In accordance with one embodiment, an apparatus includes first logic to detect coordinates of feature points from first images; second logic to detect coordinates of feature points from second images, the first and second images corresponding to scanned swaths on a wafer; third logic to generate reference coordinates based on the coordinates of the feature points of the first and second images; and fourth logic to detect a defect of the wafer by comparing the first and second images based on the reference coordinates. The third logic may compare the first and second images based on the reference coordinates. The apparatus includes fifth logic to provide information of the defect to a photolithography system; and sixth logic to change a photolithography condition based on the information. The apparatus may also include a controller to control a photolithography process on the wafer based on the changed photolithography condition. The wafer includes a plurality of dies.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise indicated. Accordingly, various changes in form and details may be made without departing from the spirit and scope of the embodiments set forth in the claims.

What is claimed is:

1. An inspection device, comprising:
a first processor to detect first coordinates of first feature points from first images in a first image set, the first coordinates of the first feature points including 1-st to n-th first coordinates, where n is a natural greater than one;
a second processor to detect second coordinates of second feature points from second images in a second image set, the second coordinates of the second feature points including 1-st to n-th second coordinates; and
a server to generate 1-st to n-th reference coordinates based on the 1-st to n-th first coordinates and the 1-st to n-th second coordinates, respectively, and to transmit the 1-st to n-th reference coordinates to the first processor and the second processor, wherein the first and second image sets correspond to a same scanned swath on a wafer, wherein:
the 1-st reference coordinate is generated using the 1-st first coordinate and the 1-st second coordinate, and
the n-th reference coordinate is generated using the n-th first coordinate and the n-th second coordinate.

2. The inspection device as claimed in claim 1, wherein the first processor is to:
align locations of the 1-st to n-th first coordinates to correspond to the 1-st to n-th reference coordinates respectively, and
align remaining coordinates of the first images in accordance with movement of the locations of the 1-st to n-th first coordinates to generate first aligned images.

3. The inspection device as claimed in claim 2, wherein the first processor is to:
set one of the first aligned images as a reference image,
set the remaining images, except the reference image among the first images aligned, as target images, and
align the target images based on the reference image.

4. The inspection device as claimed in claim 1, wherein the second processor is to:
align locations of the 1-st to n-th second coordinates to correspond to the 1-st to n-th reference coordinates respectively, and align remaining coordinates of the second images in accordance with movement of the locations of the 1-st to n-th second coordinates to generate second aligned images.

5. The inspection device as claimed in claim 4, wherein the second processor is to:
set one of the aligned second images as a reference image,
set the remaining images, except the reference image among the aligned second images, as target images, and
align the target images based on the reference image.

6. The inspection device as claimed in claim 1, wherein:
each of X coordinates of the 1-st to n-th reference coordinates is calculated as an average value of each of X coordinates of the 1-st to n-th first coordinates and each of X coordinates of the 1-st to n-th second coordinates, and
each of Y coordinates of the 1-st to n-th reference coordinates is calculated as an average value of each of Y coordinates of the 1-st to n-th first coordinates and each of Y coordinates of the 1-st to n-th second coordinates.

7. The inspection device as claimed in claim 1, wherein:
each of X coordinates of the 1-st to n-th reference coordinates is calculated as a median value of each of X coordinates of the 1-st to n-th first coordinates and each of X coordinates of the 1-st to n-th second coordinates, and
each of Y coordinates of the 1-st to n-th reference coordinates is calculated as a median value of each of Y coordinates of the 1-st to n-th first coordinates and each of Y coordinates of the 1-st to n-th second coordinates.

8. The inspection device as claimed in claim 1, wherein:
the same inspection swath is one of a plurality of inspection swaths that extend in a first direction on a plurality of dies of the wafer, and
the remaining inspection swaths, except the one inspection swath among the plurality of inspection swaths, extend in a second direction perpendicular to the first direction on the plurality of dies of the wafer.

9. An inspection method, comprising:
receiving, from an image sensor, a plurality of image sets generated by scanning one inspection swath of a plurality of inspection swaths on a test wafer;
detecting, by a first processor, first coordinates of first feature points from first images in a first image set among the plurality of image sets, the first coordinates of the first feature points including 1-st to n-th first coordinates, where n is a natural number greater than one;
detecting, by a second processor, second coordinates of second feature points from second images in a second image set among the plurality of image sets, the second coordinates of the second feature points including 1-st to n-th second coordinates;
generating, by a server, 1-st to n-th reference coordinates based on the 1-st to n-th first coordinates and the 1-st to n-th second coordinates, respectively;
generating, by the first processor, first aligned images by aligning locations of the 1-st to n-th first coordinates to correspond to the 1-st to n-th reference coordinates; and
generating, by the second processor, second aligned images by aligning locations of the 1-st to n-th second coordinates to correspond to the 1-st to n-th reference coordinates, wherein:
the 1-st reference coordinate is generated using the 1-st first coordinate and the 1-st second coordinate, and
the n-th reference coordinate is generated using the n-th first coordinate and the n-th second coordinate.

10. The method as claimed in claim 9, further comprising:
setting, by the first processor, one of the first aligned images as a reference image;
setting, by the first processor, remaining images, except the reference image among the first aligned images, as target images; and
generating, by the first processor, new first images by aligning the target images based on the reference image.

11. The method as claimed in claim 10, further comprising:
setting, by the second processor, one of the second aligned images as a reference image;
setting, by the second processor, the remaining images, except the reference image among the second aligned images, as target images; and
generating, by the second processor, new second images by aligning the target images based on the reference image.

12. The method as claimed in claim 11, further comprising:
storing, by a memory of an inspection device, the new first images and the new second images.

13. The method as claimed in claim 11, further comprising:
detecting, by the server, defects of the test wafer by comparing the new first images with the new second images.

14. The method as claimed in claim 13, further comprising:
providing, to a photolithography system, information corresponding to the defects,
changing a photolithography condition based on information corresponding to the defects, and
performing a photolithography process on a wafer based on the changed photolithography condition.

15. The method as claimed in claim 9, wherein the aligned first coordinates and the aligned second coordinates are equal to the reference coordinates.

16. An apparatus, comprising:
first logic circuit to detect first coordinates of first feature points from first images the first coordinates of the first feature points including 1-st to n-th first coordinates, where n is a natural number greater than one;
second logic circuit to detect second coordinates of second feature points from second images, the first and second images corresponding to a same scanned swath on a wafer, the second coordinates of the second feature points including 1-st to n-th second coordinates;
third logic circuit to generate 1-st to n-th reference coordinates based on the 1-st to n-th first and second coordinates of the first and second feature points of the first and second images, respectively; and
fourth logic circuit to detect a defect of the wafer by comparing aligned first and second images based on the reference coordinates, wherein:
the 1-st reference coordinate is generated using the 1-st first coordinate and the 1-st second coordinate, and
the n-th reference coordinate is generated using the n-th first coordinate and the n-th second coordinate.

17. The apparatus as claimed in claim 16, further comprising:
fifth logic circuit to provide information of the defect to a photolithography system; and
sixth logic circuit to change a photolithography condition based on the information.

18. The apparatus as claimed in claim 17, further comprising:
   a controller to control a photolithography process on the wafer based on the changed photolithography condition.

19. The apparatus as claimed in claim 16, wherein the third logic circuit is to:
   generate the 1-st to n-th reference coordinates by calculating an average value or a median value of the 1-st to n-th first and second coordinates of the first and second feature points.

20. The apparatus as claimed in claim 16, wherein the wafer includes a plurality of dies.

* * * * *